United States Patent [19]

Jin et al.

[11] Patent Number: 5,795,836
[45] Date of Patent: Aug. 18, 1998

[54] MEDICAL NON-WOVEN FABRICS CONTAINING INORGANIC OXIDES COMPLEX POWDER

[75] Inventors: Rui Jin; Kesen Zhao; Jun Liu; Yan Jin; Qin Lei; Xinnong Li, all of Guangdong, China

[73] Assignee: Wonder & Bioenergy Hi-Tech International, Inc., Guangdong, China

[21] Appl. No.: 907,431

[22] Filed: Aug. 7, 1997

[30] Foreign Application Priority Data

Dec. 10, 1996 [CN] China .................. 96 1 21670.0

[51] Int. Cl.⁶ ............................................. D02G 3/00
[52] U.S. Cl. ............................... 442/417; 429/372
[58] Field of Search ................. 442/417; 428/372

[56] References Cited

U.S. PATENT DOCUMENTS 5,599,851  2/1997  Jin et al. .................. 521/107

FOREIGN PATENT DOCUMENTS 105271 2AA  7/1991  China .
1027983C    3/1992  China .

*Primary Examiner*—Newton Edwards
*Attorney, Agent, or Firm*—Harness, Dickey & Pierce, P.L.C.

[57] ABSTRACT

This invention concerns a medical non-woven fabric containing inorganic oxides complex powder. The inorganic oxides complex powder consists of 80–95% (weight) of $TiO_2$, 2–10% (weight) of $Al_2O_3$ and 1–10% (weight) of $SiO_2$. This medical non-woven fabric can improve microcirculation remarkably and has special effect of dephlogistication, detumescence and speeding up healing of wounds. Thus, it is suitable for supplementary treatment of tumefaction, surface wounds and fracture.

2 Claims, No Drawings

MEDICAL NON-WOVEN FABRICS CONTAINING INORGANIC OXIDES COMPLEX POWDER

This invention concerns medical non-woven fabrics containing inorganic oxides complex powder. In particular, it concerns a medical non-woven fabric containing an inorganic oxides complex powder which consists essentially of $TiO_2$, $Al_2O_3$ and $SiO_2$. This medical non-woven fabric can improve microcirculation remarkably and has the special effects of dephlogistication, detumescence and speeding up the healing of wounds, especially suitable for treatment of open wounds, fractures, soft tissue injuries, etc.

In recent years, viscose non-woven fabrics have been used as medical dressings. For example, in Medical Textiles, 3 (Mar. 1992), there is a record of chlorine-free viscoe fiber produced by Lenzing Company. This kind of viscose non-woven fabric is usually used to replace ordinary cotton gauze. Its feature is low production cost, but it has no function of providing supplementary treatment.

In addition, Chinese Patent Application CN 90102189.x disclosed a kind of infrared low-grade energy radioactive powder, a synthetic fiber mixed with this powder and articles made from the fiber. This product, making use of porcelain's feature of radiating infrared low-grade energy, has the effect of warming and keeping warmth. Additionally, it can be used as packaging material, and has the good effect of keeping freshness and anti-bacterial. However, there is no record of its function in improving microcirculation, dephlogistication and detumescence.

Furthermore, Chinese patent No. ZL 93111620.1 granted to the present applicant disclosed a kind of multi-component powder and its articles which can improve microcirculation remarkably. However, since safety and hygiene problems are not solved, it cannot be used to make medical dressings for surface wounds. Therefore, until now, there is no precedent of medical non-woven fabrics combining inorganic oxides complex powder and non-woven fabrics.

The purpose of this invention is to provide a kind of medical non-woven fabric containing inorganic oxides complex powder, which is easy to sterilize, has good hygiene characters, can be used directly for surface wounds, has good hygroscopicity, can prevent distortion, and is easy to use. Moreover, it maintains the functions of the existing multi-component powder articles by, for example, improving microcirculation, dephlogratication, detumescence, and speeding up healing of wounds.

The purpose of this invention is reached through the following embodiment. First, treat with alkali some raw cellulose materials which cannot be directly woven (eg. short cotton velvets, timbers, reeds, bagasse, etc.) to produce alkaline cellulose, which reacts with $CS_2$ to produce cellulose xanthate. Then a viscose solution is obtained by dissolving cellulose xanthate into dilute alkaline solution. The prepared multi inorganic oxides complex powder then is spread evenly into the viscose solution through a surface active agent by grinding. The viscose solution containing complex powder is sprayed with certain pressure through a spinning jet into the acid solution. Go through acid bathing, decompose cellulose xanthate and neutralize it with alkali. The viscose is then solidified into thread. Next, the steps of washing, desulfurizing, bleaching, and acid washing are undertaken and the viscose fiber containing inorganic powder is produced. Finally, make it into non-woven fabrics through hydro-entanglement. After cutting and sterilization, the final products, such as medical functional gauze, bandage, and fracture case are obtained.

In the embodiment mentioned above, the inorganic oxides complex powder mainly consists of 80–95% (weight) of $TiO_2$, 20–10% (weight) of $Al_2O_3$ and 1–10% (weight) of $SiO_2$. The diameter of the powder is less than 0.5 µm. The content of this powder in the viscose fiber is 2.5–10% (weight). The raw material of the non-woven fabrics used is viscose fiber.

Additionally, the complex powder can optionally contain the following components: CaO, $La_2O_3$, $CeO_2$, $Y_2O_3$, $ZnO_2$ and $Ag_3PO_4$. The portion of each optional component is CaO 0–5% (weight), $La_2O_3$ 0–2% (weight), $CeO_2$ 0–5% (weight), $Y_2O_3$ 0–4% (weight), ZnO 0–2% (weight), $Ag_3PO_4$ 0–0.5% (weight).

The preferred portion of the inorganic oxides complex powder in the viscose fiber is 2.5–10% (weight). Theoretically, the medical effect is a function of the inorganic powder's content, however, if the portion of inorganic powder added in the viscose fiber exceeds 10%, there will be technical problems during weaving, and the strength and spinnability will not meet the requirements. Many experiments have proven that if the content of inorganic powder in viscose fiber is less than 2.5%, the expected treatment effect will not be reached. Therefore, the suitable portion of the inorganic oxides complex powder in the viscose fiber is 2.5–10% (weight).

The following examples are used to illustrate the invention in more detail, but they are not meant to limit the scope of the invention in any way.

EXAMPLE 1

Preparation of Functional Gauze

Spread evenly by grinding through sodium dodecyl sulfonate 6–7% (by weight) of the multi-component oxides complex powder consisting of the undermentioned components into the already-prepared viscose solution, an inorganic powder viscose fiber was produced from the solution by a known method and processed this fiber into 40 g/m² mesh non-woven fabrics with hydro-entanglement. After it was subjected it to cutting and sterilization, a functional gauze was obtained.

The complex powder is composed of the following components (% is weight portion):

| | |
|---|---|
| $TiO_2$ | 90.0% |
| $SiO_2$ | 1.0% |
| $Al_2O_3$ | 2.0% |
| CaO | 0.8% |
| $La_2O_3$ | 0.5% |
| $CeO_2$ | 3.0% |
| $Y_2O_3$ | 1.4% |
| $ZnO_2$ | 1.2% |
| $Ag_3PO_4$ | 0.1% |

EXAMPLE 2

Preparation of Funtional Gauze

Example 1 was substantially repeated, with the exception that the composition of the multi-inorganic oxides complex powder mentioned in Example 1 was instead by the undermentioned one, and the weight portion of the inorganic powder in the viscose fiber was 7–8%. After 70 g/m² non-woven fabrics was cut and sterilized, a functional bandage was obtained. The complex powder is composed of the following components (% is weight portion):

| | |
|---|---|
| $TiO_2$ | 88.0% |
| $SiO_2$ | 1.5% |
| $Al_2O_3$ | 3.5% |
| CaO | 1.0% |
| $La_2O_3$ | 0.5% |
| $CeO_2$ | 3.0% |
| $Y_2O_3$ | 1.5% |
| $ZnO_2$ | 1.0% |

EFFECT-TEST EXAMPLE 1

Supplementary Effect of Functional Gauze on Swelling

Patients with joint swelling were treated with the functional gauze obtained in Example 1. Meanwhile, another group of patients were treated with ordinary cotton gauze as control. The days needed for each group to reach certain treatment effects were counted. There are 10 patients in each group. The treatment days are days on average. The test result showed that the patients treated with the functional gauze of this invention can reach the expected effect in a period ½ shorter than those treated with ordinary cotton gauze.

EFFECT-TEST EXAMPLE 2

Supplementary Effect of Functional Gauze on Surface Wounds

The functional gauze obtained in Example 1 was applied to patients with different kinds of surface wounds. Meanwhile, ordinary cotton gauze was applied to another group of patients as control. The days needed for each group to fully recover were counted. There were 10 patients in each group. The treatment days are days on average. It is shown from the result that the patients using the functional gauze of this invention can fully recover in a period ⅓–⅕ shorter than those using ordinary cotton gauze.

EFFECT-TEST EXAMPLE 3

Supplementary Effect of Functional Bandage on Fracture

Patients suffering from different fractures were treated with the functional bandage obtained in Example 2. Meanwhile another group of patients were treated with ordinary bandage as control. The days needed for each group to recover were counted. There were ten patients in each group. The treatment days are days on average. Result showed that patients treated with the functional bandage of this invention can recover in a period ¼ shorter than those treated with ordinary bandage.

It can be concluded from the above that the present medical non-woven fabrics containing inorganic oxides compounds can improve microcirculation remarkably, has special effect of dephlogistication, detumesence and speeding up healing of wounds, and is especially suitable for supplementary treatments of tumefaction, surface wounds and fracture.

We claim:

1. A medical non-woven fabric containing inorganic oxides complex powder, which is characterized in that it contains 2.5–10% (weight) of inorganic oxides complex powder, and said powder comprises 80–95% (weight) of $TiO_2$, 2–10% (weight) of $Al_2O_3$ and 1–10% (weight) of $SiO_2$.

2. The medical non-woven fabric according to claim 1, wherein the inorganic oxides complex powder further comprises optional components such as CaO, $La_2O_3$, $CeO_2$, $Y_2O_3$, ZnO, and $Ag_3PO_4$.

* * * * *